United States Patent
Rao et al.

(10) Patent No.: US 6,452,038 B1
(45) Date of Patent: Sep. 17, 2002

(54) FLUOROALKYLOXY DISPERSANT

(75) Inventors: Prabhakara Satyauolu Rao, Maplewood; Naiyong Jing, Woodbury, both of MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 100 days.

(21) Appl. No.: 09/605,211

(22) Filed: Jun. 28, 2000

(51) Int. Cl.$^7$ .................. C07C 271/00; C07C 271/12; B01F 17/22
(52) U.S. Cl. .................. 560/115; 560/24; 560/47; 560/125; 560/157; 560/172; 560/183; 516/30; 252/182.15
(58) Field of Search .................. 516/30; 560/157, 560/172, 183, 115, 125, 24, 47; 252/182.15

(56) References Cited

U.S. PATENT DOCUMENTS

| | | | |
|---|---|---|---|
| 4,094,911 A | 6/1978 | Mitsch et al. | 568/615 |
| 4,321,404 A * | 3/1982 | Williams et al. | 560/115 |
| 4,440,918 A * | 4/1984 | Rice et al. | 526/247 |
| 4,523,039 A | 6/1985 | Lagow et al. | 568/615 |
| 4,818,801 A * | 4/1989 | Rice et al. | 526/247 |
| 4,894,484 A | 1/1990 | Lagow et al. | 568/615 |
| 5,026,621 A | 6/1991 | Tsubuko et al. | 430/106.2 |
| 5,210,274 A | 5/1993 | Huth | 560/26 |
| 5,266,650 A * | 11/1993 | Guerra et al. | 526/247 |
| 5,283,148 A | 2/1994 | Rao | 430/114 |
| 5,397,669 A | 3/1995 | Rao | 430/114 |
| 5,530,053 A | 6/1996 | Rao et al. | 524/462 |
| 5,573,711 A | 11/1996 | Hou et al. | 252/572 |
| 5,604,070 A | 2/1997 | Rao et al. | 430/108.2 |
| 5,681,881 A | 10/1997 | Jing et al. | 524/368 |
| 5,753,763 A | 5/1998 | Rao et al. | 525/276 |
| 5,919,293 A | 7/1999 | Moffatt et al. | 106/31.57 |
| 5,919,866 A | 7/1999 | Rao et al. | 525/276 |

FOREIGN PATENT DOCUMENTS

| | | |
|---|---|---|
| EP | 0 594 472 A | 4/1994 |
| EP | 0 683 436 A | 11/1995 |
| WO | WO 96/31547 A | 10/1996 |
| WO | WO 97/35904 A | 10/1997 |

* cited by examiner

*Primary Examiner*—Daniel S. Metzmaier
(74) *Attorney, Agent, or Firm*—Philip Y. Dahl

(57) ABSTRACT

The present invention provides a compound according to the formula: $CH_2=C(R^1)-C(O)-R^6-NHCO_2(CH_2)_p(CF_2)_q-O-((CF_2)_aCFXO)_m(CF_2)_r-Z$ wherein each $R^1$ is independently selected from —H, —$CH_3$, —F and —Cl, wherein each $R^6$ is independently selected from substituted or unsubstituted C1–C10 alkyl, cyclic alkyl, or aryl groups, wherein each a is independently selected from 0–3, wherein each X is independently selected from —F, —$CF_3$ or —$CF_2CF_3$, wherein each p is independently selected from 1–4, each q is independently selected from 1–5, each r is independently selected from 1–5, each m is independently selected from 1–50, each Z is independently selected from —F and —$(CH_2)_sOH$, and each s is independently selected from 1–4. The present invention also provides for the use of this compound as a surfactant in highly fluorinated liquid solvents. Latexes of dispersed particles utilizing this surfactant are provided.

6 Claims, No Drawings

FLUOROALKYLOXY DISPERSANT

FIELD OF THE INVENTION

This invention relates to a compound useful as a dispersant in highly fluorinated solvents. The compound contains an ethylenic double bond by which it may be joined to another moiety, e.g. by free-radical polymerization. The compound is described by the formula: $CH_2=C(R^1)-(O)O-R^6-NHCO_2(CH_2)_p(CF_2)_q-O-((CF_2)_aCFXO)_m(CF_2)_r-Z$ wherein each $R^1$ is independently selected from —H, —$CH_3$, —F and —Cl, wherein each $R^6$ is independently selected from substituted or unsubstituted C1–C10 alkyl, cyclic alkyl, or aryl groups, wherein each a is independently selected from 0–3, wherein each X is independently selected from —F, —$CF_3$ or —$CF_2CF_3$, wherein each p is independently selected from 1–4, each q is independently selected from 1–5, each r is independently selected from 1–5, each m is independently selected from 1–50, each Z is independently selected from —F and —$(CH_2)_sOH$, and each s is independently selected from 1–4.

BACKGROUND OF THE INVENTION

U.S. Pat. No. 5,397,669 (Minnesota Mining & Manufacturing) discloses liquid toners for use with perfluorinated solvents. The patent discloses that the compositions are film-forming, allowing them to function properly as toners. ('669 at p. 8 lns. 3–5). The '669 patent discloses pigment particles bound to a polymer that is highly fluorinated in specific parts, and that includes monomer units having groups that bind polyvalent metal ions. The '669 patent also discloses pigment particles bound to a polymer that is highly fluorinated in its entirety, without requiring monomers having groups that bind polyvalent metal ions.

U.S. Pat. No. 5,530,053 (Minnesota Mining & Manufacturing) also discloses liquid toners for use with perfluorinated solvents. The toners of '053 are polymeric dyes which are highly fluorinated in specified parts and have attached chromophoric groups. The '053 patent discloses that the toner can form a latex in perfluorinated solvent, where the toner takes a core-shell form with the hydrocarbon portion in the core and the fluorocarbon portion in the shell.

U.S. Pat. No. 5,919,293 (Hewlett-Packard) discloses ink jet inks composed of colorants in Fluorinert™ solvents (Minnesota Mining & Manufacturing Co., St. Paul, Minn.), which are perfluorinated or nearly-perfluorinated alkanes.

U.S. Pat. No. 5,573,711 (Copytele) discloses the use of certain polymeric fluorosurfactants in electrophoretic image displays. The '711 patent teaches the use of Fluorad™ surfactants (Minnesota Mining & Manufacturing Co., St. Paul, Minn.), including FC-171, having the structure $R_f-SO_2N(C_2H_5)(CH_3CH_3O)_nCH_3$, where n is about 8 and $R_f$ is a fluorocarbon portion.

SUMMARY OF THE INVENTION

Briefly, the present invention provides a compound according to the formula: $CH_2=(R^1)-C(O)O-R^6-NHCO_2(CH_2)_p(CF_2)_q-O-((CF_2)_aCFXO)_m(CF_2)_r-Z$, wherein each $R^1$ is independently selected from —H, —$CH_3$, —F and —Cl, wherein each $R^6$ is independently selected from substituted or unsubstituted C1–C10 alkyl, cyclic alkyl, or aryl groups, wherein each a is independently selected from 0–3, wherein each X is independently selected from —F, —$CF_3$ or —$CF_2CF_3$, wherein each p is independently selected from 1–4, each q is independently selected from 1–5, each r is independently selected from 1–5, each m is independently selected from 1–50, each Z is independently selected from —F and —$(CH_2)_sOH$, and each s is independently selected from 1–4. Preferably each m is independently selected from 7–15. Preferably Z is —$(CH_2)_sOH$. Preferably a, p, q, r and s are each 1 and wherein X is —F.

In another aspect, the present invention provides a second compound which is a reaction product of the compound above resulting from free-radical addition to the ethylenic double bond. In particular, a non-film-forming latex of particles comprising the compound above in a highly fluorinated solvent is provided.

What has not been described in the art, and is provided by the present invention, is a reactive dispersant according to the present formula and its use in a non-film-forming latex of hydrocarbon/fluorocarbon particles dispersed in a fluorocarbon solvent useful in an electrophoretic display.

In this application:

"reacting dyes" means dyes which are covalently bound to the polymer;

"non-reacting dyes" means dyes which are not substantially incorporated into a polymer by polymerization, including every dye that is not a reacting dye;

"highly fluorinated", means containing fluorine in an amount of 40 wt % or more, but preferably 50 wt % or more and more preferably 60 wt % or more, and refers to the fluorine content of a population of chemical moieties where applicable, such as in the term, "one or more highly fluorinated macromers";

"non-fluorinated", means containing substantially no fluorine, i.e. containing fluorine in an amount of 5 wt % or less, but preferably 1 wt % or less and most preferably 0 wt %, and refers to the fluorine content of a population of chemical moieties where applicable, such as in the term, "one or more non-fluorinated free-radically-polymerizable monomers";

"C(number)" refers to a chemical moiety containing the indicated number of carbon atoms;

"(meth)acrylate" means acrylate and methacrylate; and

"substituted" means, for a chemical species, substituted by conventional substituents which do not interfere with the desired product or process, e.g., substituents can be alkyl, alkoxy, aryl, phenyl, halo (F, Cl, Br, I), cyano, etc.

It is an advantage of the present invention to provide a dispersant for use in highly fluorinated solvents and which is particularly useful in making a latex of non-film-forming dye-bearing particles.

DETAILED DESCRIPTION OF THE PREFERRED EMBODIMENTS

The present invention provides a compound according to the formula: $CH_2C(R^1)-C(O)O-R^6-NHCO_2(CH_2)_p(CF_2)_q-O-((CF_2)_nCFXO)_m(CF_2)_r(CH_2)_sOH$, wherein each $R^1$ is independently selected from —H, —CH, —F and —Cl, wherein each $R^6$ is independently selected from substituted or unsubstituted C1–C10 alkyl, cyclic alkyl, or aryl groups, wherein each a is independently selected from 0–3, wherein each X is independently selected from —F, —$CF_3$ or —$CF_2CF_3$, wherein each p is independently selected from 1–4, each q is independently selected from 1–5, each r is independently selected from 1–4, each s is independently selected from 1–4, each m is independently selected from 1–50. Preferably each m is independently selected from 7–15. Preferably a, p, q, r and s are each 1 and wherein X is —F.

A non-film-forming latex employing the dispersant according to the present invention comprises a highly fluorinated liquid solvent and dispersed particles comprising a polymer comprising units according to formula I:

(I)

wherein each (fcp) is independently selected from highly fluorinated polymer chains which may terminate at the —A═ group of another unit according to formula I so as to form a polymer molecule that contains two or more A groups linked by (fcp) groups; wherein each Q is independently selected from —H and straight or branched non-fluorinated polymer chains (hcp), wherein no more than one Q of each unit according to formula I may be —H, and wherein each (hcp) may terminate at the —A═ group of another unit according to formula I so as to form a polymer molecule that contains two or more A groups linked by (hcp) groups. Preferably some of the (hcp) groups are branched due to the inclusion of polyfunctional crosslinkers. Preferably the particles contain reacting or non-reacting dyes. Preferably the particles additionally contain charging agents.

Preferably the —A═ group is the moiety according to formula II:

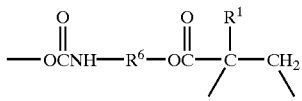
(II)

wherein each $R^1$ is independently selected from —H, —$CH_3$, —F and —Cl; wherein each —$R^6$— is independently selected from divalent substituted or unsubstituted C1–C10 alkylene, cyclic alkylene, or arylene groups. The (fcp) moieties may terminate at A groups at one or both ends. The (hcp) moieties may terminate at A groups at one or both ends, or at more than two ends if the (hcp) moiety is branched due to the inclusion of a crosslinker. Thus it is contemplated that a single molecule may contain numerous A groups linked by (hcp) groups.

The fluorocarbon polymer (fcp) portions are preferably highly fluorinated macromers. Preferred macromers include macromers of monomers selected from fluoroalkyl acrylates, fluoroalkyl methacrylates, fluoroalkyl haloacrylates and fluoroalkyl halomethacrylates. Preferably these macromers are fluoropolymer chains comprising units according to formula III:

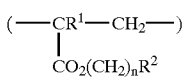
(III)

where each $R^1$ is independently selected from —H, —$CH_3$, —F and —Cl; each n is independently selected from integers from 1 to 10; and each $R^2$ is selected independently from: highly fluorinated substituted or unsubstituted C1–C20 alkyl, cyclic alkyl, or aryl groups; —$N(R^3)SO_2R^4$, where each —$R^3$ is selected independently from —H and substituted or unsubstituted C1–C8 alkyl, and where each —$R^4$ is selected independently from highly fluorinated substituted or unsubstituted C1–C20 alkyl, cyclic alkyl, or aryl groups. Preferably —$R^1$ groups are —H or —$CH_3$. Preferably n is 1 or 2, more preferably 1. Preferably —$R^2$ is a highly fluorinated C1–C20 alkyl group, more preferably a highly fluorinated C1–C8 alkyl group. In another preferred embodiment, the —$R^2$ groups of the (fcp) are a mixture selected from highly fluorinated C1–C8 alkyl groups and —$N(R^3)SO_2R^4$, where —$R^3$ is selected from C1–C8 alkyl groups —$R^4$ is selected from highly fluorinated C1–C8 alkyl groups.

In another preferred embodiment, (fcp) are polyfluoroalkylethers, preferably those comprising one or more units according to the formula —$(CF_2)_aCFXO$—, where a is 0–3, but most preferably 1, and X is —F, —$CF_3$ or —$CF_2CF_3$ but most preferably —F. More preferred polyfluoroalkylethers comprise units according to the formula —$CF_2CF_2O$—. Preferred polyfluoroalkylethers are those according to the formula —$NHCO_2(CH_2)_p(CF_2)_q$—O—$(CF_2CF_2O)_m(CF_2)_r(CH_2)_sOH$ when (fcp) is monovalent or —$NHCO_2(CH_2)_p(CF_2)_q$—O—$(CF_2CF_2O)_m(CF_2)_r(CH_2)_sCO_2NH$— when (fcp) is divalent, where p is 1–4, q is 1–5, r is 1–5, s is 1–4, m is 1–50. Preferably q is 1–2. Preferably r is 1–2. Preferably s is 1–2. Preferably p is equal to s and q is equal to r. Preferably m is 5–20 and more preferably 7–15. The chain may alternately terminate with —F in place of —$(CH_2)_sOH$ in the formula above.

The hydrocarbon polymer (hcp) groups are preferably non-fluorinated macromers (including co-macromers) of (meth)acrylate and other ethylenically unsaturated monomers such as styrenes. The hydrocarbon polymer (hcp) macromers are preferably polymers or copolymers of one or more of the following preferred monomers. Preferred monomers include monomers according to the formula: $CH_2$═$CR^1$—$C(O)OR^2$, where —$R^1$ is hydrogen or methyl and —$R^2$ is selected from C1–C20 substituted or unsubstituted, straight-chain or branched or cyclic, alkyl or aryl groups. Especially preferred monomers of this group include ethyl (meth)acrylate, methyl (meth)acrylate and isobornyl (meth)acrylate, butyl (meth)acrylate, isobutyl (meth)acrylate, t-butyl (meth)acrylate, hydroxypropyl (meth)acrylate, acetoacetoxyethyl (meth)acrylate. Preferred monomers also include styrene or substituted styrene monomers such as methylstyrene.

The hydrocarbon polymer (hcp) portions preferably include non-fluorinated crosslinkers, and are therefore branched. Preferred crosslinkers include polyacrylates such as PEG Diacrylate with a molecular weight of preferably between 200 and 2000.

In order to improve resistance to film-forming, preferably the (hcp) portion of the particles contains one or more of: crosslinkers, cyclic or polycyclic monomers, aromatic monomers, and C12 or larger substituted or unsubstituted alkyl monomers. More preferably the (hcp) portion of the particles contains one or more of: crosslinkers, cyclic or polycyclic monomers and aromatic monomers.

The hydrocarbon polymer (hcp) portions may also include reacting dyes which are incorporated into the polymer chain as monomer units. Such reacting dyes contain a chromogenic portion and a reactive portion, which are not exclusive of each other. Preferably the reactive portion is a free-radically-polymerizable group, such as a vinyl or (meth) acrylate group. In one preferred embodiment, a free-radically-polymerizable group is added to a dye by derivatization with isocyanatoethyl methacrylate. In one procedure, the dye is suspended in a solvent such as FC-75 by sonication and an equivalent of isocyanatoethyl methacrylate is added dropwise, followed by two drops of dibutyltin dilaurate catalyst and continued sonication and agitation for 1 hour. A preferred reacting dye and method of preparation is disclosed in the examples below.

The dispersed particles may also include non-reacting dyes. The non-reacting dyes have greater affinity for the particles than for the solvent and are therefore contained in the particles. Preferably the non-reacting dyes have greater affinity for the (hcp) portions of the particle than for the (fcp) portions or the solvent. Preferred non-reacting dyes are disclosed in the examples below. The particles according to the present invention preferably contain no particulate pigments.

Without wishing to be bound by theory, it is believed that the particles take the form of a hydrocarbon-polymer-rich core and a fluoropolymer-rich shell. It is believed that most dyes are incorporated in the core due to compatibility with the hydrocarbon material of the core. Thus it is believed that reducing the fluoropolymer content of the particles improves the optical properties of the particle by allowing easier access to the dyed core. In addition, it is believed that reducing the fluoropolymer content of the particles can improve the particle's resistance to film formation. Preferably the particles are composed of 40–99 percent by weight non-fluorinated hydrocarbon polymer and 1–60 percent by weight highly fluorinated fluoropolymer. More preferably the particles are composed of 60–99 percent by weight non-fluorinated hydrocarbon polymer. More preferably the particles are composed of 1–40 percent by weight highly fluorinated fluoropolymer. Most preferably the particles are composed of 1–10 percent by weight highly fluorinated fluoropolymer. However, greater fluoropolymer content is acceptable as particle size is decreased. In particles of less than 200 nm average diameter, the particles are preferably composed of 10–40 percent by weight highly fluorinated fluoropolymer, more preferably 10–25 percent by weight highly fluorinated fluoropolymer.

The dispersed particles may also include charging agents. The charging agent renders the particle mobile under the influence of an electric field. In addition, the charge imparted to the particles by the charging agent creates an electrostatic repulsion between particles which improves resistance to film formation. Like non-reacting dyes, the charging agent has a greater affinity for the particles than for the solvent and is therefore contained in the particles. Preferably the charging agent has a greater affinity for the (hcp) portions of the particle than for the (fcp) portions or the solvent. The charging agent is preferably cationic, more preferably a quaternary ammonium cation. Preferred charging agents include 1-ethyl-3-methyl-1H-imidazolium bis (trifluoromethylsulfonylamide), which may be prepared as disclosed in the examples below; $(C_4H_9)_3NHOC(O)—C_7F_{15}$; $(C_3H_7)_4N^+$ $^-OC(O)—C_7F_{15}$; $(C_4H_9)_4N^+$ $^-OC(O)—C_9F_{19}$; $C_7F_{15}—CO_2H$; and combinations thereof.

Latexes according to the present invention preferably demonstrate a high conductance as measured by the method described in the examples below. Measured conductance is taken to reflect the charge/mass ratio (charge density) of the particles in suspension, whether imparted by the charging agent or inherent in the particle itself. Preferred latexes according to the present invention have a conductance of 1 picomho/cm or more, more preferably 4 picomho/cm or more, and most preferably 9 picomho/cm or more. However, lower conductance is acceptable when particle size is decreased. In particles of less than 200 nm average diameter, conductance is preferably 0.1 picomho/cm or more.

The average diameter (particle size) for the dispersed particles of the latex is preferably measured by the method described in the examples below. Smaller particles are preferred for a number of reasons, including greater and faster mobility and lesser tendency to form a film. Preferably the particles have an average diameter of 1000 nm or less, more preferably 350 nm or less, more preferably 300 nm or less, more preferably 250 nm or less, and most preferably 200 nm or less. The seed method of latex formation described below has been found to produce exceptionally fine particles. That method and the resulting fine particles are preferred.

The solvent may be any suitable highly fluorinated solvent. The solvent is preferably a fluorocarbon, especially a branched or unbranched, cyclic or non-cyclic fluoroalkane. Preferred solvents include FLUORINERT™ fluorinated solvents available from 3M Company, St. Paul, Minn. Two especially preferred solvents are FLUORINERT FC-75, a perfluorinated $C_8$ solvent, CAS No. [86508-42-1], and FLUORINERT FC-84, a perfluorinated $C_7$ solvent, CAS No. [86508-42-1].

The density of particles in solvent (solids content) may be any level at which the dispersion is stable and does not significantly coagulate. For use of the latex in an electrophoretic display, the solids content may be any level that allows proper functioning over repeated cycles. Preferably, the solids content is less than 10 wt %, more preferably less than 5 wt %, and most preferably less than 2 wt %.

The latexes according to the present invention may be incorporated into electrophoretic displays. A typical display comprises two planar electrodes defining a thin gap between them which holds the latex. When a sufficient voltage of the correct polarity is applied, the suspended particles are drawn out of suspension and onto one electrode. That electrode, which is substantially transparent, forms the inner surface of a viewing glass, such that the particles form an image viewed through the glass. In contradiction to the characteristics of an electrostatic toner, which must form a permanent image under analogous conditions, the latex of the present invention must return to suspension when the voltage is removed or reversed.

The latexes of the present invention have high resistance to film formation when used in electrophoretic display devices. To determine resistance to film formation, an actual device may be used or a breadboard device as described in the examples below. Latexes of any solids content may be tested but preferably the solids content is 1 wt %. The device is preferably used in a normal manner, alternately applying and removing (or reversing) the typical use voltage. The voltage should be sufficient to remove particles from suspension and create an image when applied. Preferably the latexes are non-film-forming to the extent that they redisperse completely (by appearance to the naked eye) after at least twenty cycles, more preferably after at least 100 cycles, and most preferably after at least 10,000 cycles. Without wishing to be bound by theory, it is believed that the resistance to film formation demonstrated by the latexes of the present invention is aided by incorporation of crosslinkers, by the choice of high Tg monomers such as 3,4 methyl styrene, isobornyl acrylate, by reduction of the fluoropolymer content resulting in a thinner outer shell zone, by increasing the electrostatic charge (conductance) of the particles, by exclusion of particulate pigments, which may be replaced with dyes. The latexes and particles according to the present invention are preferably non-film-forming due to one or more of the preceding conditions.

Any suitable method of synthesis which results in the latexes according to the present invention may be used. One method of making latexes according to the present invention is illustrated by the syntheses of latexes L1 to L15 in the Examples below. In this method, a highly fluorinated macromer is synthesized by polymerization and the macromer is then derivatized to add a terminal polymerizable group. The macromer is then polymerized together with non-fluorinated monomers, preferably using a polymerization initiator and optionally a crosslinker, to form the latex particle. Reacting dyes must be added prior to polymerization. Non-reacting dyes and charging agents may be added at any stage, but are preferably added prior to polymerization. All reactions preferably take place in a highly fluorinated solvent. Preferably the reaction mixture is no more concentrated than 15 wt % reactants relative to the amount of solvent.

A more preferred method of making the latexes of the present invention is designated the seed method, and is illustrated by the syntheses of latexes L16 to L18 in the Examples below. In this method the polymerization to form the latex particles is performed in two steps. First, the highly fluorinated macromer and a fraction of the non-fluorinated monomers are polymerized with agitation to form a population of seed particles. The weight ratio of highly fluorinated macromer to non-fluorinated monomer is preferably between 1:2 and 9:1. In the second step, the remainder of the non-fluorinated monomers are added. The amount of additional monomer is preferably at least 10% of the weight of the seed particles, and preferably not more than 20 times the weight of the seed particles. Preferably the reaction mixture is no more concentrated than 15 wt % reactants relative to the amount of solvent. The seed method can achieve a smaller average particle diameter, preferably 250 nm or less, and more preferably 200 nm or less.

This invention is useful in electrophoretic image displays.

Objects and advantages of this invention are further illustrated by the following examples, but the particular materials and amounts thereof recited in these examples, as well as other conditions and details, should not be construed to unduly limit this invention.

EXAMPLES

Materials

The following materials were used in these examples. Where not otherwise noted, all chemicals and reagents may be available from Aldrich Chemical Co., Milwaukee, Wis.

TRIGONOX™ 21C-50 (50%) is a trade designation for a thermal free radical polymerization initiator available from Akzo Nobel Chemicals, Inc., Watertown, Conn.

FLUORINERT™ materials are fluorinated solvents available from 3M Company, St. Paul, Minn. FLUORINERT FC-75 is a perfluorinated $C_8$ solvent, CAS No. [86508-42-1]. FLUORINERT FC-84 is a perfluorinated $C_7$ solvent, CAS No. [86508-42-1].

FLUORAD™ materials are fluorinated surfactants/surface modifiers available from 3M Company, St. Paul, Minn. FLUORAD FC-740 is 50% fluoroaliphatic polymeric esters in naphtha, CAS No. [64742-94-5]. FLUORAD FC-171 is a mixture of 87–93% fluorinated alkylalkoxylate, CAS no. [68958-61-2]; 4–10% fluorinated alkylsulfonamide, CAS no. [4151-50-2]; and 2–4 % fluorinated alkylsulfonamide, CAS no. [68958-60-1]. FLUORAD FC-722 is a 2% solution of fluorinated copolymer in perfluorinated $C_{5-18}$ solvent, CAS No. [86508-42-1]. FLUORAD FC-430 is a 98.5% solution of fluoroaliphatic polymeric esters in toluene. FLUORAD FC-189 is 2-(N-butylperfluorooctanesulfonamido)ethyl acrylate. FLUORAD FC-170C is 68 wt % perfluoroalkylsulfonamido oxyethylene adduct [29117-08-6], 12 wt % polyethylene glycol, 7 wt % water, approx. 5 wt %. perfluoroalkylsulfonamido oxyethylene adduct [56372-23-7], and approx. 5 wt. % perfluoroalkylsulfonamido oxyethylene adduct [68298-79-3].

Lithium bis(trifluoromethylsulfonyl)amide is available under the trade designation HQ-115 from 3M Company, St. Paul, Minn.

1H,1H-perfluoroalkyl methacrylate is available under the trade designation L-1987 from 3M Company, St. Paul, Minn. 1H,1H-perfluorooctyl acrylate is available from Exfluor Corp., Austin, Tex.

PEG (400) diacrylate is a polyethylene glycol diacrylate available from Polysciences, Inc., Los Angeles, Calif.

Dibutyltin dilaurate, isocyanatoethyl methacrylate, vinyl trifluoroacetate, 3-mercapto-1,2-propanediol, 2,2'-azobis (isobutyronitrile), isobornyl methacryl ate, methyl methacrylate, ethyl methacrylate, 1-ethyl-3-methyl-1H-imidazolium chloride, 2,2,2-trifluoroethyl acrylate, and dimethylaminoethyl methacrylate are available from Aldrich Chemical Co., Milwaukee, Wis. and other general chemical suppliers.

Mercaptopropyltrimethoxysilane was obtained from United Chemical Technologies, Inc., Petrarch Systems, Bristol , Pa.

OXSOL™ R 2000 is α,α,α-trifluoromethyltoluene, available from Occidental Chemical Corp., Dallas, Tex.

FLUORAD™ FC-3275 is a blue dye in perfluorinated $C_7$–C8 solvents available from 3M Company of St. Paul, Minn.

GENSOLVE™ 2000 is dichlorofluoromethane CAS No. 1717-00-6; also labeled as hydrochlorofluorocarbon HCFA-141b.

Synthesis of Fluoromacromer Solvents with Polyanerizable Terminal Groups

Fluorocarbon macromers designated FMD-1, FMD-2, FMD-3 and FMD-4, were synthesized using the components listed in Table I and the procedure described following.

A mixture of the monomers indicated in Table I was dissolved in the indicated solvent (Fluorinert™ FC-75 or FC-84) to make a 50% (by weight) solution, in a three-neck flask equipped with a reflux condenser, nitrogen inlet tube and addition funnel. The specified amount of 3-mercapto-1,2-propanediol was added as a chain transfer agent. The mixture was flushed with nitrogen for 20 minutes. The specified amount of the indicated polymerization initiator (Trigonox 21C-50 or 2,2'-azobisisobutyronitrile) was added. The mixture was then polymerized for 12 hrs at 75° C. A second increment of the initiator in the same amount was added and the mixture was polymerized for another 12 hrs at 75° C. Next, the reaction temperature was raised to 85° C. for 1 hr to destroy residual initiator. The polymer dispersion was then cooled to room temperature.

Finally, the terminal group monomer, isocyanatoethyl methacrylate (IEM), was added with thorough mixing in the indicated amount, which is stoichiometrically equimolar to the chain transfer agent, followed by two drops of dibutyltin dilaurate to complete the reaction of the isocyanate with one of the two hydroxyl end groups of the polymer.

TABLE I

| Fluorinert ™ Solvent | FMD-1 FC-84 | FMD-2 FC-84 | FMD-3 FC-75 | FMD-4 FC-75 |
|---|---|---|---|---|
| Monomers: | | | | |
| 1H,1H-Perfluoroalkyl methacrylate | | | | 93.6 g |

TABLE I-continued

| Fluorinert™ Solvent | FMD-1 FC-84 | FMD-2 FC-84 | FMD-3 FC-75 | FMD-4 FC-75 |
|---|---|---|---|---|
| 1H,1H-Perfluorooctyl acrylate | 136.23 g | 136.23 g | 136.23 | |
| FLUORAD™ FC-189 | 45.4 g | | 45.4 g | 31.2 g |
| Dimethylaminoethyl methacrylate | | 13.6 g | | |
| Vinyl trifluoroacetate | | | | 25 g |
| 2,2,2-trifluoroethyl acrylate | | | | 25 g |
| Chain Transfer Agent: 3-mercapto-1,2-propanediol | 0.3225 g | 0.3225 g | 0.2 g | 0.215 g |
| Initiators: | | | | |
| Trigonox™ 21C-50 | 1 g | 1 g | 0.5 g | 0.32 g |
| 2,2'-azobisisobutyronitrile | | | | 0.33 g |
| Terminal Group Monomer: Isocyanatoethyl methacrylate | 0.925 g | 0.925 g | 0.60 g | 0.62 g |

Synthesis of Charging Agent, 1-Ethyl-3-methyl-1H-imidazolium bis(Trifluoromethylsulfonylamide)

1-Ethyl-3-methyl-1H-imidazolium chloride (49.0 g) was dissolved in 285.0 g deionized water to form a 1M solution. 127.8 ml of this solution was combined with 36.7 g lithium bis(trifluoromethylsulfonyl)amide and 50 ml dichloromethane in a flask with a magnetic stir bar. The solution was allowed to stir overnight, then transferred to a separatory funnel, where the aqueous phase was washed three times with 10 ml of dichloromethane. The three dichloromethane phases were combined and the dichloromethane was removed under reduced pressure. The recovered material was used without further purification.

Synthesis of Non-Film Forming White Acrylic Latex Particles

White (non-dye-bearing) acrylic latexes, designated L1, L2, L3, L4 and L5, were synthesized using the components listed in Table II and the procedure described following.

A mixture of the indicated acrylic monomers, optionally including PEG 400 diacrylate crosslinker as indicated, was suspended in 500 ml of Fluorinert™ solvent FC-75 along with the indicated fluoromacromer solvent, FMD-1 or FMD-4, in a three-neck flask equipped with a reflux condenser, nitrogen inlet tube and addition funnel. Where indicated, a mixture of the indicated Fluorad™ surfactants was added to enhance the stability of the dispersion. Where indicated, a charging agent, 1-ethyl-3-methyl-1H-imidazolium bis(trifluoromethylsulfonylamide), was added. A polymerization initiator, Trigonox™ 21C-50, was added in an amount of 0.1–0.2 % by weight of the reaction mixture. This reaction mixture was flushed with nitrogen for 20 minutes and then the mixture was polymerized for 12 hrs at 75° C. A second increment of the initiator in the same amount was added and the mixture was polymerized for another 12 hrs at 75° C. The resulting latex was then filtered through a thickly folded cheese cloth to remove agglomerated particles.

The resulting latexes contained a solids content of about 5 wt %. Solids content was measured by evaporating a known weight of the latex to dryness by heating to 100° C. in a vacuum oven and weighing of the remaining dry solids.

Particle size and size distribution, reported in Table II, were measured using a Coulter N4 PLUS dynamic light scattering photometer (Coulter Corp., Miami, Fla.) with a measuring range of 3 nm to 3 $\mu$m. Particle size and size distributions were obtained at the high dilution range set by the instrument.

Conductance, reported in Table II, was measured using a Scientifica Model 627 conductivity meter (available from Scientifica of Princeton, N.J.) using a stainless steel concentric cylinder probe. A frequency of 18 Hz was applied to the outer cylinder. The conductivity of the liquid sample was determined by measuring the current between the outer cylinder and the inner cylinder. Higher conductance is indicative of higher charge/mass ratio, which indicates that the particles may be more easily moved by application of an electric field.

Film-forming characteristics were tested in a breadboard display device, which included a transparent indium tin oxide electrode coated on an essentially planar high refractive index display glass opposite an essentially planar metal counter electrode. The gap between electrodes was 5–10 $\mu$m. The volume between the display glass electrode and the counter electrode was filled with the latex to be tested and a voltage of 10 volts was applied for less than a second, driving the latex particles to the display glass. After the voltage was removed, non-film-forming latexes redispersed in the solvent, whereas film-forming latexes fully or partially remained on the display glass. Non-film-forming latexes redisperse completely (by appearance to the naked eye) after at least twenty cycles. Film forming latexes typically would not rediperse in the first or second cycle. Toner compositions are unable to redisperse after a single cycle, consistent with their role in electrophotographic processes.

Latexes L1–L5 were found to be non-film forming.

TABLE II

| | L1 | L2 | L3 | L4 | L5 |
|---|---|---|---|---|---|
| Monomers: | | | | | |
| Ethyl Methacrylate | 20 g | | | 15 g | |
| Methyl Methacrylate | | 20 g | | 15 g | |
| Isobornyl Methacrylate | | | 20 g | | 20 g |
| PEG 400 Diacrylate | 4 g | 4 g | | | |

TABLE II-continued

|  | L1 | L2 | L3 | L4 | L5 |
|---|---|---|---|---|---|
| FC Macromer: |  |  |  |  |  |
| FMD-4 |  |  | 12.5 g |  |  |
| FMD-1 | 1.5 g | 1.5 g |  | 12.5 g | 15 g |
| Surfactant Mixture: Fluorad ™ surfactants | none | none | FC-430, 2 g FC-170C, 3 g | FC-740, 0.6 g FC-171, 0.5 g FC-722, 2.5 g | FC-430, 2.0 g FC-170C, 2.5 g |
| Charging Agent: | none | none | 0.5 g | 0.5 g | none |
| Conductance (picomho/cm) | 1.74 | 4.8 | 9.5 | 4.5 | 9.5 |
| Particle Size {distribution} | 302 nm {narrow} | 575 nm {broad} | 800 nm {broad} | 280 nm {narrow} | not measured |

Addition of Charging Agent to Non-Film Forming Acrylic Latex Particle Dispersions Acrylic latexes L1, L2, L4 and L5 were diluted to 1 wt % dispersions in FC-75 solvent. Additional charging agent was added to the dispersion in the amount indicated and the conductivity was measured by the method described above.

TABLE III

| Conductance (picomho/cm) | L1 | L2 | L4 | L5 |
|---|---|---|---|---|
| No additional charging agent | 1.74 | 4.8 | 4.6 | 9.5 |
| 0.02% additional charging agent | 1.83 | 4.4 | 4.6 | 9.3 |
| 0.04% additional charging agent | 1.85 | 4.3 | 4.7 | 9.2 |
| 0.10% additional charging agent | 902 | 220 | 550 | 1398 |

Synthesis of Non-Film Forming Dye-Bearing Acrylic Latex Particles

Dye-bearing acrylic latexes, designated L6 (Cyan), L7 (Cyan), L8 (Red), L9 (Yellow), L10 (Yellow), L11 (Violet), L12 (Magenta), L13 (Cyan) and L14 (Magenta), were synthesized using the components listed in Table IV and the procedure described following.

A mixture of the indicated acrylic monomers, optionally including PEG 400 diacrylate crosslinker as indicated, was suspended in 500 ml of Fluorinert™ solvent FC-75 along with 2.0 g of fluoromacromer solvent FMD-1. (IBA= isobornyl acrylate, MMA=methyl methacrylate, EMA=ethyl methacrylate). For L6 (Cyan) only, 3 g of a mixture of Fluorad™ surfactants (2:3 by weight FC-430 and FC-171) was added to enhance the stability of the dispersion. The indicated hydrocarbon-soluble dye was dissolved in the monomer mixture along with a small quantity of Genesolve™ 2000 (essentially $CH_3CCl_2F$; Allied Signal, Morristown, N.J.) to facilitate and accelerate the solvation of the dye. A polymerization initiator, Trigonox™ 21C-50, was added in an amount of 0.1–0.2 % by weight of the reaction mixture. This reaction mixture was flushed with nitrogen for 20 minutes and then the mixture was polymerized for 12 hrs at 75° C. A second increment of the initiator in the same amount was added and the mixture was polymerized for another 12 hrs at 75° C. The resulting latex was then filtered through a thickly folded cheese cloth to remove agglomerated particles.

Dyes were modified as follows:

PECHS salts of Basic Violet (C.I. 42555) and Basic Blue (C.I. 1) were made by exchanging cations for PECHS:

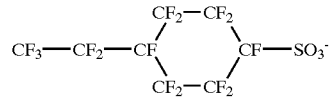

Derivatized Solvent Yellow 18 (C.I. 12740) was a reactive dye incorporating a function polymerizable with the acrylic monomers. The derivatized dye was made as follows: 1 g of Solvent Yellow 18 (C.I. 12740) was suspended in 25 ml of FC-75 perfluorinated fluid by sonication. Isocyanatoethyl methacrylate (0.566g ) was added dropwise to the dye suspension under sonication, followed by two drops of dibutyltin dilaurate catalyst. After an hour under sonication and agitation, the suspension was filtered, washed with FC-84 and dried under vacuum below 40° F., the dry solid being the derivatized dye.

It was found that the dyes were substantially entirely contained in the latex particles, presumably in the hydrocarbon polymer core. Unreacted dye was found in a coagulum obtained after filtering the latex through cheesecloth as described.

The resulting latexes contained a solids content of about 5 wt %, measured as described above.

Particle size and conductance were measured as described above. Latexes L6–L14 were each tested and proved to be non-film forming.

TABLE IV

|  | L6 (Cyan) | L7 (Cyan) | L11 (Violet) | L13 (Cyan) | L8 (Red) | L12 (Magenta) | L14 (Magenta) | L9 (Yellow) | L10 (Yellow) |
|---|---|---|---|---|---|---|---|---|---|
| Dye | 0.25 g Solvent Blue (C.I. 97) | 0.25 g Solvent Blue (C.I. 97) | 0.2 g Basic Violet (C.I. 42555) PECHS salt | 0.2 g Basic Blue (C.I. 1) PECHS salt | 0.25 g Solvent Red 23 (C.I. 26100) | 0.2 g Magenta Solvent Dye (CAS 58559-02-7) | 0.2 g Magenta Solvent Dye (CAS 58559-02-7) | 1.6 g Derivatized Solvent Yellow 18 (C.I. 12740) | 1.75 g Derivatized Solvent Yellow 18 (C.I. 12740) |
| Monomer | 25 g MMA | 25 g MMA | 25 g MMA | 25 g MMA | 25 g IBA | 25 g MMA | 25 g MMA | 25 g EMA | 25 g MMA |

TABLE IV-continued

|  | L6 (Cyan) | L7 (Cyan) | L11 (Violet) | L13 (Cyan) | L8 (Red) | L12 (Magenta) | L14 (Magenta) | L9 (Yellow) | L10 (Yellow) |
|---|---|---|---|---|---|---|---|---|---|
| Crosslinker: 5 g PEG (400) diacrylate | None | 5 g | 5 g | 5 g | 5 g | 5 g | 5 g | None | 5 g |
| Conductance (picomho/cm) | 1.0 | 3.4 | 2.4 | 3.8 | 44 | 2.5 | 2.8 | 4.5 | 1.7 |
| Particle Size (distribution) | 255 nm (narrow) | 290 nm (narrow) | 300 nm (narrow) | 240 nm (narrow) | 240 nm (narrow) | 280 nm (narrow) | 300 nm (narrow) | 300 nm (narrow) | 260 nm (narrow) |

Synthesis of Very Fine Non-Film Forming White Acrylic Latex Particles by Seed Method A latex of very fine white (non-dye-bearing) acrylic particles, designated L16, was synthesized using the seed method described following.

2.5 g of FMD-1 and 2.5 g methylstyrene (a mixture of 3- and 4-methyl isomers obtained from Aldrich Chemical Company, Milwaukee, Wis., Cat. No. 30,898-6) were added to 250 ml of Fluorinert™ solvent FC-75, in a three-neck flask equipped with a reflux condenser, nitrogen inlet tube and addition funnel. One gram of the polymerization initiator, Trigonox™ 21C-50, was added. This reaction mixture was flushed with nitrogen for 15 minutes and then the mixture was polymerized for about 100 minutes at 80° C. with vigorous stirring using a magnetic stir bar. A white turbid suspension of seed polymer particles resulted. The temperature of the reaction mixture was lowered to 70° C. with continued stirring and another 1 part Trigonox™ 21C-50 was added. An additional 10 g of the methylstyrene was added dropwise via an addition funnel into the stirred reaction mixture over a period of 2 hours while the reaction temperature was kept at 70° C. After addition of monomer was complete the polymerization was allowed to continue for another 16 hours. The resulting latex was then filtered through a thickly folded cheese cloth to remove agglomerated particles. The latex had an average particle size of 220 nm and a conductance of 0.1 picomho/cm, measured as described above.

Synthesis of Very Fine Non-Film Forming Dye-Bearing Acrylic Latex Particles by Seed Method The synthesis of L16, preceding, was repeated except that 0.15 g of Solvent Blue (C.I. 97) dye were dissolved in the 10 g of methylstyrene monomer added dropwise to the seed suspension. The resulting cyan colored latex, designated L17 (Cyan), had an average particle size of 375 nm; and a conductance of 0.1 picomho/cm, measured as described above.

Additional Synthesis of Very Fine Non-Film Forming Dye-Bearing Acrylic Latex Particles by Seed Method The synthesis of very fine dye-bearing latex L18 (Cyan), using the seed method described following, was repeated three times.

In a reaction flask, 7.5 g of FMD-1 and 2.5 g ethyl acrylate were added to 250 parts ml of Fluorinert™ solvent FC-75, in a three-neck flask equipped with a reflux condenser, nitrogen inlet tube and addition funnel. One gram of the polymerization initiator, Trigonox™ 21 C-50, was added. This reaction mixture was flushed with nitrogen for 30–45 minutes. The temperature was rapidly raised to 80° C. and then the mixture was polymerized for 2 hrs with vigorous stirring using a magnetic stir bar. After two hours, a mixture of 10 g of isobornyl acrylate and 0.2 g of Solvent Blue (C.I. 97) dye was added dropwise via an addition funnel into the stirred reaction mixture over a period of 1 hour while the reaction temperature was kept at 70° C. An additional 1 g of Trigonox™ 21 C-50 was added. After addition of monomer was complete the polymerization was allowed to continue for another 16–20 hours. The resulting latex was then filtered through a thickly folded cheese cloth to remove agglomerated particles. Particle size and conductance were measured as described above. In three repetitions of this synthesis, the three resulting latexes were found to have average particle sizes of 140, 160 and 175 nm respectively. Conductance was measured as 0.79 picomho/cm for one of the L18 (Cyan) latexes.

Synthesis of Perfluoropolyether Fluoromacromer Dispersant

A fluoromacromer dispersant designated FMD-5 based on a perfluoropolyether was synthesized as follows.

The perfluoroether diol HO—$CH_2CF_2$—O—($CF_2CF_2O)_n$—$CF_2CH_2$—OH was synthesized, where n is a distribution (nominally 10) and the diol has an average molecular weight of 1250. Polyethylene glycol (ave. m.w. 600)(Aldrich Chemical Co., Milwaukee, Wis.) was mixed with approximately two equivalents of $CH_3C(O)Cl$ at ambient temperature in the presence of two equivalents of triethylamine to form a diacetate. The diacetate was then fluorinated by direct fluorination, such as disclosed in U.S. Pat. No. 4,523,039 (Lagow et al.). The resulting fluorinated acetate was mixed with excess amount of methanol whereupon it reacted to give methyl esters such as $CH_3O(CO)CF_2O$—$(CF_2CF_2O)_{n-2}$—$CF_2(CO)OCH_3$. These methyl esters were then reduced to the corresponding dihydroalcohols, such as $HOCH_2CF_2O$—$(CF_2CF_2O)_{n-2}$—$CF_2CH_2OH$, by reaction with approximately two equivalents of $NaBH_4$. The resulting mixture was distilled under reduced pressure and a 1250 m.w. fraction collected.

To 35 g of this perfluoroether diol (m.w. 1250) in a covered amber jar was added dropwise 4.34 g (aprox. 1 equivalent) of isocyanatoethyl methacrylate (m.w. 155) to obtain a milky liquid. When the milky liquid turned clear, indicating the completion of the reaction between the hydroxyl and isocyanate, two drops of dibutyltin dilaurate were added to the reaction mixture.

Synthesis of Acrylic Latex Particles Using FMD-5 Perfluoropolyether Fluoromacromer Acrylic latexes designated L19 (Cyan) and L20 (Near-White) were synthesized as follows.

For L19(Cyan), 5 g of FMD-5 was combined with 12.5 g methylstyrene (a mixture of 3- and 4-methyl isomers obtained from Aldrich Chemical Company, Milwaukee, Wis., Cat. No. 30,898-6), 5 g of Gensolve™ 2000, 0.2 g Solvent Blue (C.I. 97) and 250 g of Fluorinert™ solvent FC-75, in a three-neck flask equipped with a reflux condenser, nitrogen inlet tube and addition funnel. A polymerization initiator, Trigonox™ 21C-50, was added in the amount of 1 g. This reaction mixture was flushed with nitrogen for 30 minutes and then the mixture was polymerized for 6 hrs at 75° C. A second increment of the initiator in the same amount was added and the mixture was polymerized for another 20 hrs at 75° C. The resulting latex was then filtered through a thickly folded cheese cloth to remove agglomerated particles.

The resulting cyan colored latex, designated L19 (Cyan), had an average particle size of 172 nm, measured as described above.

For L20 (Near-White), the same procedure was followed except that the cyan dye was replaced with 0.2 g of Magenta Solvent Dye (CAS 58559-02-7). The resulting latex, designated L20 (Near-White), was a near-white pale pink color and had an average particle size of 170 nm, measured as described above.

Both L19 (Cyan) and L20 (Near-White) are observed to be non-film-forming.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

We claim:

1. A compound according to the formula:

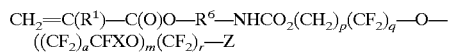

wherein each $R^1$ is independently selected from —H, —$CH_3$, —F and —Cl, wherein each $R^6$ is independently selected from substituted or unsubstituted C1–C10 alkyl, cyclic alkyl, or aryl groups, wherein each a is independently selected from 0–3, wherein each X is independently selected from —F, —$CF_3$ or —$CF_2CF_3$, wherein each p is independently selected from 1–4, each q is independently selected from 1–5, each r is independently selected from 1–5, each m is independently selected from 1–50, and Z is —$(CH_2)_s$OH, where each s is independently selected from 1–4.

2. A compound according to the formula:

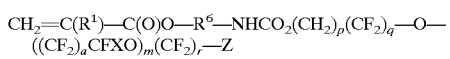

wherein each $R^1$ is independently selected from —H, —$CH_3$, —F and —Cl, wherein each $R^6$ is independently selected from substituted or unsubstituted C1–C10 alkyl, cyclic alkyl, or aryl groups, wherein each a is independently selected from 0–3, wherein each X is independently selected from —F, —$CF_3$ or —$CF_2CF_3$, wherein each p is independently selected from 1–4, wherein each q is independently selected from 1–5, wherein each r is independently selected from 1–5, wherein each m is independently selected from 7–15, wherein each Z is —$(CH_2)_s$OH, and wherein each s is independently selected, from 1–4.

3. A compound according to the formula:

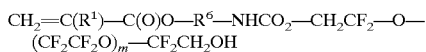

wherein each $R^1$ is independently selected from —, —$CH_3$, —F and —Cl, wherein each $R^6$ is independently selected from substituted or unsubstituted C1–C10 alkyl, cyclic alkyl, or aryl groups, and wherein m is selected from 7–15.

4. A solution of the compound according to claim 1 in a highly fluorinated solvent.

5. A solution of the compound according to claim 2 in a highly fluorinated solvent.

6. A solution of the compound according to claim 3 in a highly fluorinated solvent.

* * * * *

UNITED STATES PATENT AND TRADEMARK OFFICE
CERTIFICATE OF CORRECTION

PATENT NO. : 6,452,038 B1
DATED : September 17, 2002
INVENTOR(S) : Rao, Prabhakara S.

It is certified that error appears in the above-identified patent and that said Letters Patent is hereby corrected as shown below:

Title Page,
Item (57), ABSTRACT,
Line 2, "—C(O)—$R^6$" should be -- —C(O)O—$R^6$ --.

Column 1,
Lines 9-10, "—(O)O—$R^6$" should be -- —C(O)O—$R^6$ --.
Line 58, "($R^1$)—C(O)O—$R^6$" should be -- C($R^1$)—C(O)O—$R^6$ --.

Column 2,
Line 54, "$CH_2C(R^1)$—C(O)O—$R^6$" should be -- $CH_2$=C($R^1$)—C(O)O—$R^6$ --.
Line 55, "$((CF_2)_nCFXO)$" should be -- $((CF_2)_aCFXO)$ --.
Line 56, "—CH, —F" should be -- —$CH_3$, —F --.
Line 63, "from 1 - 4, each s" should be -- from 1 - 5, each s --.

Column 4
Line 6, -- , and wherein each -- should be inserted following "groups".
Line 19, "Preferably q " should be -- Preferably p is 1 - 2. Preferably q --.
Line 20, "r" should be -- q --.
Line 20, insert -- Preferably r is 1 to 2. -- preceding "preferably".

Column 5
Line 48, "NHOC" should be -- N:HOC --.

Column 6
Line 55, "isobomyl" should be -- isobornyl --.

Column 8
Line 13, "metha crylate" should read -- methacrylate --.
Line 25, "C8" should be -- $C_8$ --.
Line 32, "Polyanerizable" should read -- Polymerizable --.

Column 9
Line 6, "136.23" should read -- 136.23 g --.
Line 22, "butyronitnitrile" should read -- butyronitrile --.

Column 10
Line 49, "rediperse" should be -- redisperse --.

Column 12
Line 37, "25" should be -- ~25 --.

UNITED STATES PATENT AND TRADEMARK OFFICE
CERTIFICATE OF CORRECTION

PATENT NO. : 6,452,038 B1
DATED : September 17, 2002
INVENTOR(S) : Rao, Prabhakara S.

It is certified that error appears in the above-identified patent and that said Letters Patent is hereby corrected as shown below:

Column 16
Line 30, "from —, —CH$_3$," should be -- from —H, —CH$_3$, --.

Signed and Sealed this

Twenty-second Day of June, 2004

JON W. DUDAS
*Acting Director of the United States Patent and Trademark Office*